United States Patent
Sidebotham et al.

(10) Patent No.: US 9,655,924 B2
(45) Date of Patent: May 23, 2017

(54) SYSTEM FOR TREATING EAR INFECTIONS

(71) Applicant: BioMedtrix, LLC, Boonton, NJ (US)

(72) Inventors: Christopher G. Sidebotham, Mendham, NJ (US); Alan Mundell, Edmonds, WA (US)

(73) Assignee: BioMedtrix, LLC, Whippany, NJ (US)

( * ) Notice: Subject to any disclaimer, the term of this patent is extended or adjusted under 35 U.S.C. 154(b) by 32 days.

(21) Appl. No.: 14/681,701

(22) Filed: Apr. 8, 2015

(65) Prior Publication Data

US 2015/0283175 A1    Oct. 8, 2015

Related U.S. Application Data

(60) Provisional application No. 61/976,999, filed on Apr. 8, 2014.

(51) Int. Cl.

| | |
|---|---|
| *A61K 33/38* | (2006.01) |
| *A61K 31/60* | (2006.01) |
| *A61K 45/06* | (2006.01) |
| *A61K 36/752* | (2006.01) |
| *A61K 31/56* | (2006.01) |
| *A61K 9/00* | (2006.01) |

(52) U.S. Cl.
CPC ............ *A61K 33/38* (2013.01); *A61K 9/0046* (2013.01); *A61K 31/56* (2013.01); *A61K 31/60* (2013.01); *A61K 36/752* (2013.01); *A61K 45/06* (2013.01)

(58) Field of Classification Search
CPC .............................. A61K 33/38; A61K 9/0046
See application file for complete search history.

(56) References Cited

U.S. PATENT DOCUMENTS

| | | | |
|---|---|---|---|
| 2007/0081958 A1 | 4/2007 | Bechert et al. | |
| 2008/0275113 A1* | 11/2008 | Huetter | A01N 25/30 514/494 |
| 2014/0271881 A1* | 9/2014 | Allart | A61K 9/0017 424/489 |

(Continued)

FOREIGN PATENT DOCUMENTS

| | | | | |
|---|---|---|---|---|
| WO | WO2013017807 | * | 2/2013 | ............. A61K 31/07 |

OTHER PUBLICATIONS

Bio Epiderm, "MicroSilver BG™," available on the internet at http://www.bioepiderm.com/upload/downloads/20080124_Broschre_Einzelseiten_englisch.pdf, 2008 (12 pages).

(Continued)

*Primary Examiner* — Rachael Bredefeld
(74) *Attorney, Agent, or Firm* — Klarquist Sparkman, LLP

(57) ABSTRACT

Disclosed herein are compositions for treatment of ear infection (such as bacterial and/or yeast infection) in human or veterinary subjects. In some embodiments the compositions include silver microparticles, for example about 0.1% silver microparticles, about 0.2% silver microparticles, or about 0.4% silver microparticles. Also disclosed are methods for treating ear infection in a subject utilizing one or more of the disclosed compositions, for example sequential application of compositions including about 0.1% silver microparticles, about 0.2% silver microparticles, and about 0.4% silver microparticles to the ear canal of the subject. In some examples, one or more of the disclosed compositions are provided in a kit.

18 Claims, 8 Drawing Sheets

(56) References Cited

U.S. PATENT DOCUMENTS

2016/0015031 A1* 1/2016 Pesaro ............... A61K 8/35
424/65

OTHER PUBLICATIONS

Bio Gate, "MicroSilver BG-Tec™," Product Information Sheet, 2009 (3 pages).
Bio Gate, "HyMedic™ 4000," Product Information Sheet, 2009 (3 pages).

* cited by examiner

FIG. 1A

Left Ear
*(Before)*

Left Ear
*(Following application of THERAPY)*

*Following completion of FLUSH, RINSE & THERAPY*

SYSTEM FOR TREATING EAR INFECTIONS

CROSS REFERENCE TO RELATED APPLICATION

This application claims the benefit of U.S. Provisional Application No. 61/976,999, filed Apr. 8, 2014, which is incorporated herein in its entirety.

FIELD

This disclosure relates to compositions and methods for treating ear infections, particularly in veterinary subjects.

BACKGROUND

Ear infections (otitis) in humans and animals can be frequent and difficult to manage with antibiotics. Microbes such as yeast (*Malassezia*) and bacterial infections (such as *Staphylococci* or *Pseudomonas*) are present in animals and are the most frequent reason to visit a veterinarian. In some cases the infection is difficult to treat or becomes resistant to antibiotics, leaving very few medical options to resolve the infection. In animals for example, when the infection cannot be managed by oral and/or topical antibiotics, total ear canal ablation (removal of the ear canal) becomes the last resort procedure. This procedure reduces or even eliminates the animal's ability to hear in the ablated ear.

SUMMARY

Disclosed herein are non-antibiotic compositions and methods for treatment of ear infection (such as bacterial and/or yeast infection) in human or veterinary subjects. In particular examples, the disclosed compositions and methods are for treatment of ear infection in companion animals or livestock (such as dogs, cats, horses, cattle, sheep, or pigs). In some embodiments the compositions include silver microparticles, for example about 0.1% silver microparticles, about 0.2% silver microparticles, or about 0.4% silver microparticles.

Also disclosed are methods for treating ear infection in a subject utilizing one or more of the disclosed compositions. In some embodiments, the methods include applying one or more of a composition including at least 0.1% silver particles, a composition including at least 0.2% silver microparticles, and a composition including at least 0.4% silver microparticles to the ear canal of a subject with an ear infection. In one particular example, the method includes sequentially applying a composition including at least 0.1% silver microparticles, a composition including at least 0.2% silver microparticles, and a composition including at least 0.4% silver microparticles to the ear canal of a subject with an ear infection.

Finally, one or more of the compositions disclosed herein are provided as a kit for treating ear infections. In one embodiment, the kit includes at least one container including a composition containing about 0.1% silver microparticles, at least one container including a composition containing about 0.2% silver microparticles, at least one container including a composition containing about 0.4% silver microparticles, or a combination of two or more thereof.

The foregoing and other features of the disclosure will become more apparent from the following detailed description, which proceeds with reference to the accompanying figures.

BRIEF DESCRIPTION OF THE DRAWINGS

Figure 1A:
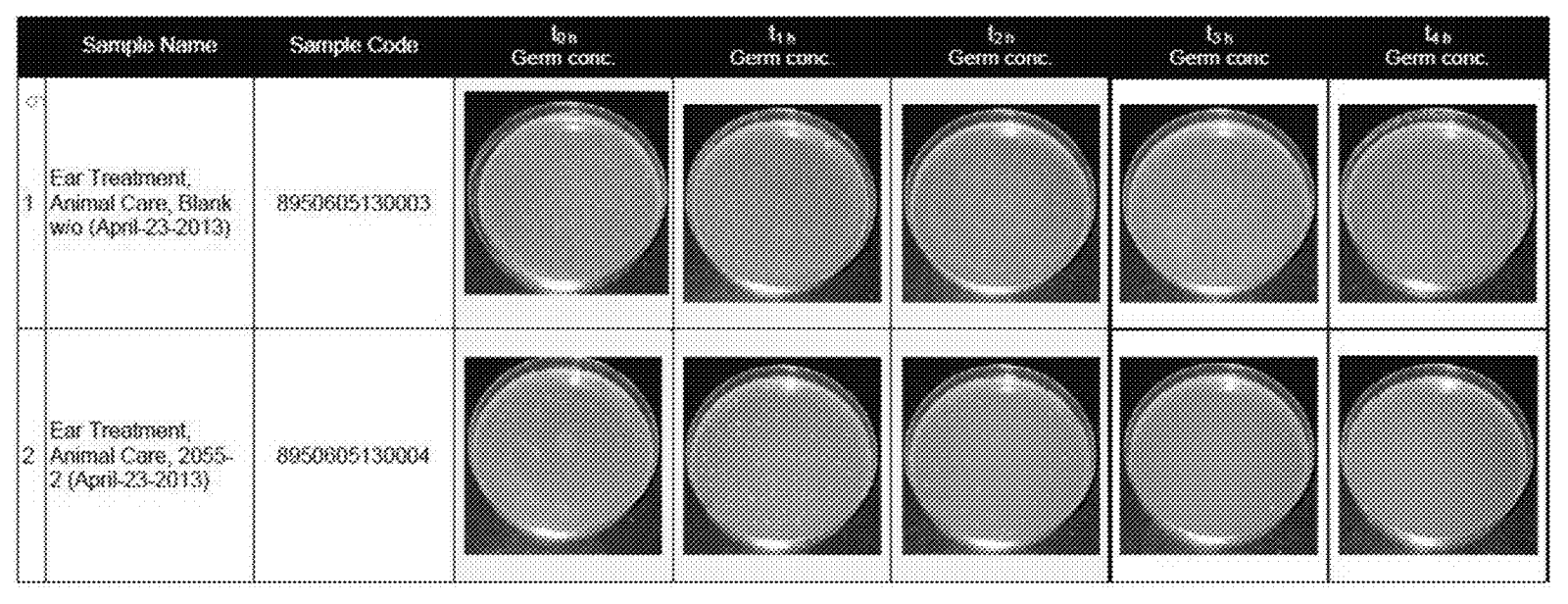

FIGS. 1A-1E are a series of panels showing efficacy of 0.2% silver microparticles in reducing yeast or bacterial growth and viability. FIG. 1A: *Malassezia pachydermatis* (DSM 6172); FIG. 1B: *Pseudomonas aeruginosa* (DSM 939/ATCC 15442); FIG. 1C: *Staphylococcus aureus* (DSM 21979); FIG. 1D: *Staphylococcus pseudintermedius* (DSM 20373/ATCC 29663); FIG. 1E: *Streptococcus* spp. (DSM 20480/ATCC 33317). Plates were treated with Santé Nurturing Spray (SantéAnimal Care, Boonton, N.J.) with or without 0.2% silver microparticles.

DETAILED DESCRIPTION

Figure 1B:
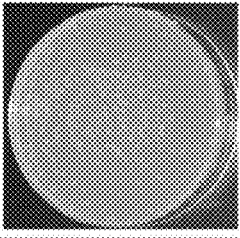
Figure 1C:
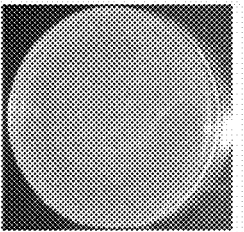
Figure 1D:
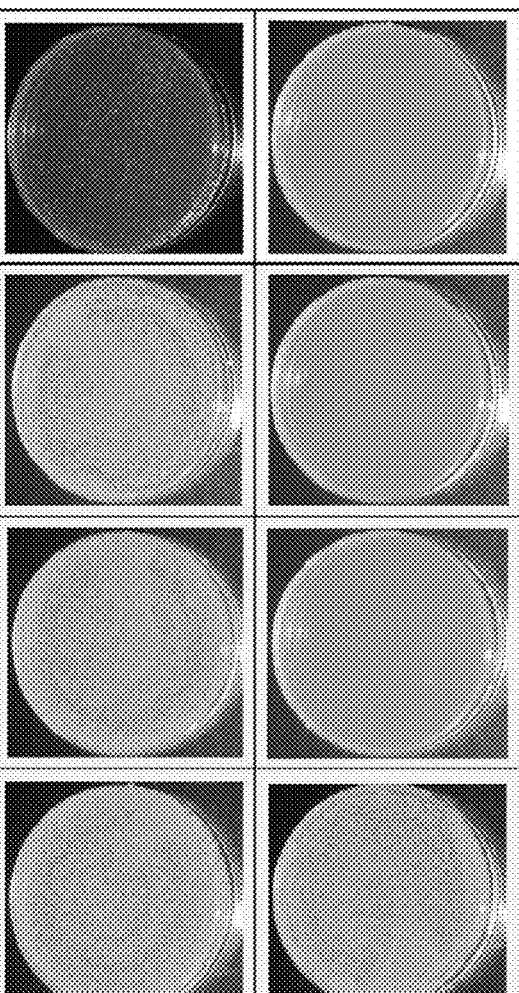
Figure 1E:
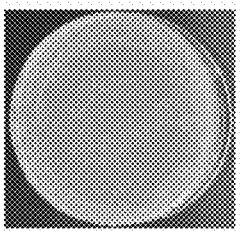

Ear infection is the most common reason for veterinary visits in companion animals. First line treatment for ear infection typically includes ear cleaning and topical or oral antibiotics or antifungal agents. However, it can be difficult to achieve effective concentrations in the ear tissue with oral antibiotics or antifungals. In some cases, the infection becomes a chronic or recurrent infection that cannot be effectively treated with antibiotic or antifungal agents. For example, the causative agents may become resistant to antibiotic or antifungal agents. In cases of severe chronic infection, ear canal ablation has been the only effective treatment; however, this severely compromises hearing or even renders the animal deaf.

Disclosed herein are compositions including silver microparticles and their use for treating ear infection. The silver microparticles in the compositions disclosed herein remain in contact with the ear canal for an extended period of time (for example hours to days), producing silver ions, which have antimicrobial activity. Furthermore, the compositions and methods disclosed herein do not utilize antibiotics and thus can be effective against antibiotic-resistant bacteria and can improve or resolve chronic ear infection, avoiding surgical intervention such as ear canal ablation.

I. TERMS

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Ear Infection (Otitis):

An overgrowth of bacteria or yeast (fungus) in the ear canal. Symptoms include ear discomfort or pain, redness, swelling, odor, and/or discharge. In veterinary subjects, an ear infection may be indicated by rubbing or shaking the head, head tilt, or scratching at the affected ear. Ear infection is typically accompanied by inflammation, wax buildup, and formation of a biofilm.

Agents that commonly cause ear infection (for example chronic ear infection) include bacteria and fungi, such as *Staphylococcus aureus*, *Staphylococcus intermedius*, *Staphylococcus pseudintermedius*, *Pseudomonas aeruginosa*, *Streptococcus* spp., *Micrococcus* spp., *Malassezia pachydermatis*, *Candida* spp., or *Aspergillus* spp.

Effective Amount:

An amount of an agent or composition that alone, or together with a pharmaceutically acceptable carrier and/or one or more additional agents, induces the desired response without adverse effects. Effective amounts of an agent can be determined in many different ways, such as assaying for a reduction in bacterial or fungal growth or viability, a reduction or amelioration of one or more symptoms of a subject with ear infection, or delay (or even prevention) of recurrent ear infection. Effective amounts also can be determined through various in vitro, in vivo or in situ assays. In some examples, an effective amount is an amount that provides a concentration of silver microparticles (or silver ions produced by the silver microparticles) on the ear canal membranes sufficient to kill or inhibit microbial growth.

Microparticle:

A microscale particle with a size that is measured in micrometers, for example, a microscopic particle that has at least one dimension of less than about 700 μm. In some examples, a microparticle has at least one dimension from about 0.1 μm to about 700 μm (such as about 0.3 μm to about 300 μm or about 1 μm to about 100 μm). Examples of microparticles include metal microparticles, such as silver microparticles.

Pharmaceutically Acceptable Carrier:

A diluent, adjuvant, excipient, or vehicle with which a therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is an exemplary carrier. Saline solutions, blood plasma medium, aqueous dextrose, and glycerol solutions can also be employed as liquid carriers. The medium may also contain conventional pharmaceutical adjunct materials such as for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. Pharmaceutically acceptable carriers include those described in *Remington: The Science and Practice of Pharmacy*, The University of the Sciences in Philadelphia, Editor, Lippincott, Williams, & Wilkins, Philadelphia, Pa., 21$^{st}$ Edition (2005).

Subject:

Living multi-cellular vertebrate organisms, a category that includes human and non-human mammals, such as veterinary subjects (such as dogs, cats, horses, sheep, cattle, pigs, and other livestock).

II. METHODS AND SYSTEMS FOR TREATING EAR INFECTION

Disclosed herein are methods and systems for treating, inhibiting, or even preventing ear infection in a subject (for example a veterinary subject). In some examples, ear infection in the subject includes otitis externa, otitis media, or both. In particular examples, the ear infection is a chronic ear infection, such as an ear infection that recurs or is resistant to conventional treatment (such as topical antibiotic or antifungal agents or systemic antibiotics or antifungals). The ear infection may be caused by bacteria or fungi, including but not limited to *Staphylococcus aureus*, *Staphylococcus intermedius*, *Staphylococcus pseudintermedius*, *Pseudomonas aeruginosa*, *Streptococcus* spp., *Streptococcus bovis*, *Streptococcus suis*, *Micrococcus* spp., *Malassezia pachydermatis*, *Mycoplasma* spp., *Mycoplasma bovis*, *Mannheimia haemolytica*, *Pasteurella multocida*, *Histophilus somni*, *Neisseria* spp., corynebacteria, *Arcanobacterium pyogenes*, *Candida* spp., or *Aspergillus* spp.

The methods include applying an effective amount of one or more compositions including silver microparticles to the ear canal. In particular embodiments, the compositions include silver microparticles at a concentration of at least about 0.1%, such as about 0.1%, 0.2%, 0.3%, 0.4%, or 0.5%. The silver microparticles generate silver ions (for example, in an aqueous environment), which have antimicrobial properties.

In some examples, one or more of the disclosed compositions are aqueous solutions. In other examples, one or more of the disclosed compositions are lotions, gels, creams, or ointments. For example, the type and viscosity of the compositions are selected based on their use. In some examples, the compositions including 0.1% silver microparticles or 0.2% silver microparticles have a viscosity that allows them to flow out of the ear, which is desirable for their use in flushing and rinsing the ear canal (discussed below). In other examples, the composition including 0.4% silver microparticles has a higher viscosity (for example, as compared to the "flush" and "rinse" compositions) providing for the composition (or the silver microparticles in the composition) to remain in the ear in contact with the ear canal membrane, permitting continued anti-microbial activity from the generation of silver ions. One of skill in the art can select appropriate viscosities for the compositions disclosed herein. The compositions may also include suitable buffers, carriers, preservatives and/or other components, optionally including additional therapeutic agents. The compositions are described in detail in Section III, below.

In some embodiments of the disclosed methods, a composition including about 0.1% silver microparticles is applied to the ear canal of a subject with ear infection. In some examples, the composition including about 0.1% silver microparticles (referred herein in some examples as the "flush" composition), is a cleansing formulation for breaking up and/or removing debris, ear wax, and biofilms present in the ear canal of the subject. Therefore, in some examples, an effective amount of the flush composition (for example, about 3-5 ml if the subject is a dog) is applied to the ear canal and the ear is massaged externally. The flush composition is applied using a dropper in some examples. Excess flush composition and any external loosened debris are removed from the ear by wiping, for example with a cotton ball, swab, or soft cloth. In some examples, treatment with the flush composition is applied at least once per day (for example two, three, or more times a day). In other examples, treatment with the flush composition is applied every other day, twice per week, once per week, every other week, or once per month. The flush composition can be applied one, two, or three times per treatment, for example to increase the effectiveness of the composition for breaking up debris, ear wax, and/or biofilms in the ear canal of the subject. The number of applications of flush composition in a treatment is selected based on the amount of wax build-up and biofilm present in the subject's ear and the overall condition of the ear, with multiples flushes (for example, two, three, or more) used if the build-up or overall condition (e.g., inflammation) is severe, while a single flush can be used for subjects with mild build-up and less severe overall condition.

In other embodiments of the disclosed methods, a composition including about 0.2% silver microparticles is applied to the ear canal of a subject with ear infection. In some examples, the composition including about 0.2% silver microparticles (referred herein in some examples as the "rinse" composition), is a rinsing formulation for removing debris, ear wax, and biofilms present in the ear canal of the subject. Therefore, in some examples, an effective amount of the rinse composition is applied to the ear canal (for example, about 3-5 ml if the subject is a dog) and the ear is massaged externally. The rinse composition is applied using a dropper in some examples. Excess rinse composition is removed from the ear by wiping, for example with a cotton ball, swab, or soft cloth. In some examples, treatment with the rinse composition is applied at least once per day (for example two or three times a day). In other examples, treatment with the rinse composition is applied every other day, twice per week, once per week, every other week, or once per month. In some examples, the rinse composition is applied following treatment with the flush composition. The rinse composition can be applied once or twice per treatment, for example to increase the effectiveness of the composition for removing debris, ear wax, and/or biofilms from the ear canal of the subject. For example, the rinse composition application can be repeated if substantial amounts of debris and wax are removed with the first rinse, to facilitate removing as much debris as possible (for example, prior to therapy composition application).

In additional embodiments of the disclosed methods, a composition including about 0.4% silver microparticles is applied to the ear canal of a subject with ear infection. In some examples, the composition including about 0.4% silver microparticles (referred herein in some examples as the "therapy" composition), is a therapeutic formulation for treating or inhibiting ear infection with microbial agents (such as bacteria and/or fungi) present in the ear canal of the subject. Therefore, in some examples, an effective amount of the therapy composition is applied to the ear canal and the ear is massaged externally to work the therapy composition into the ear canal. In some examples, the therapy composition is applied to the ear canal of the subject using a syringe, such as a syringe with a flexible tip. The therapy composition is left in contact with the ear canal of the subject (e.g., it is not wiped away after application). Thus, in some examples, the therapy composition (or the silver microparticles in the therapy composition) remains in contact with the surfaces of the ear canal (e.g., for at least 5 minutes, at least 10 minutes, at least 30 minutes, at least 1 hour, at least 2 hours, at least 4 hours, or more), gradually releasing silver ions and inhibiting or reducing microbial growth and/or viability.

In particular embodiments, one or more additional therapeutic agents are included in the therapy composition. For example, an anti-inflammatory agent, such as a corticosteroid (for example dexamethasone) can be included in the therapy composition. In other examples, an antibiotic or antifungal agent could be included in the therapy composition. A skilled clinician can select the type and amount of additional therapeutic agents to be added to the therapy composition, if needed.

The amount of therapy composition applied to the ear canal depends on the size of the subject and can be selected by an experienced clinician. If the subject is a dog, in some examples, the amount of therapy solution used is selected based on the size of the dog (Table 1).

TABLE 1

Amount of therapy solution for canine subjects

| Size of Dog | Weight | Therapy Composition Applied (mL) |
|---|---|---|
| Small | <14 lbs | 1-2 |
| Medium | 14-40 lbs | 2-3 |
| Large | 40-100 lbs | 3-4 |
| Giant | >100 lbs | >4 |

In some examples, treatment with the therapy composition is applied at least once per day (for example two or three times a day). In other examples, treatment with the therapy composition is applied every other day, twice per week, once per week, every other week, or once per month. In some examples, the therapy composition is applied following treatment with the flush composition and/or following treatment with the rinse composition. In other examples, the therapy composition is applied following ear cleaning with another cleaning solution (such as saline; Douxo® Micellar cleansing solution, Sogeval Laboratories, Irving, Tex.; Epi-Otic® ear cleanser, Virbac Corporation, Fort Worth, Tex.; TrizUltra™+Keto flush, Dechra Veterinary Products, Overland Park, Kans.).

In some embodiments, the disclosed methods for treating ear infection in a subject include a three-step system using the disclosed flush composition, rinse composition, and therapy composition. In one example, the method includes applying an effective amount of the flush composition including about 0.1% silver microparticles to the ear canal of the subject, massaging the ear externally, and wiping away excess flush composition and debris with a cotton ball or other soft material. This step can optionally be repeated one or more times. Next, an effective amount of the rinse composition including about 0.2% silver microparticles is applied to the ear canal, the ear is massaged externally, and excess rinse composition is wiped away with a cotton ball or other soft material. Finally, an effective amount of the therapy composition including about 0.4% silver microparticles is applied to the ear canal of the subject and the ear is externally massaged to work the therapy composition into the ear canal. The therapy composition is not wiped away after application. This three step system for treating ear infection can be administered to the subject at least once per day (such as twice per day). In other examples, the flush and rinse compositions are utilized once daily and the therapy composition is applied twice daily. In still further examples, the flush, rinse, and therapy compositions are applied every other day, twice a week, once a week, every other week, or once per month. A skilled clinician can determine the appropriate treatment frequency based on the condition to be treated (for example, the type or severity of ear infection), the subject, and whether the treatment is for active ear infection or maintenance/prevention of recurrence once an infection is controlled.

In other embodiments, the disclosed methods for treating ear infection include applying an effective amount of the flush composition including about 0.1% silver microparticles to the ear canal of the subject, massaging the ear externally, and wiping away excess flush composition and debris with a cotton ball or other soft material. This step can optionally be repeated one or more times. Next, an effective amount of the rinse composition including about 0.2% silver microparticles is applied to the ear canal, the ear is massaged externally, and excess rinse composition is wiped away with a cotton ball or other soft material. In some examples, the flush and rinse compositions are utilized once daily. In still further examples, the flush and rinse compositions are applied every other day, twice a week, once a week, every other week, or once per month. A skilled clinician can determine the appropriate treatment frequency based on the condition to be treated (for example, the type or severity of ear infection), the subject, and whether the treatment is for active ear infection or maintenance/prevention of recurrence once an infection is controlled. This two-step system can be utilized in cases of mild ear infection, removing wax build-up and biofilm (which may be less severe) and leaving behind remnant silver microparticles which can treat the mild infection. In more severe cases, application of the therapy composition (for example in the three-step system discussed above) may be required for effective treatment of the infection.

III. COMPOSITIONS FOR TREATING EAR INFECTION

Disclosed herein are compositions containing silver microparticles that can be used to treat ear infection in a subject (such as a veterinary subject, for example dogs or cats). The compositions contain at least 0.1% silver microparticles (such as 0.1%-0.5% silver microparticles) and in some examples are aqueous solutions. As described in Section II, the compositions can be used separately or in combination as a system for treating ear infection in a subject.

In some embodiments, the microparticles used in the disclosed compositions are silver microparticles, such as microparticles produced from high purity metallic silver. The silver microparticles have a highly porous, sponge-like structure with a large surface area. In other examples, the microparticle is a core-shell microparticle, having a core with a shell or coating of silver. Silver microparticles and methods for producing them are known in the art. In some examples, silver microparticles are produced by vaporization of silver (such as medical grade silver wire) using thermal plasma. In some examples, the microparticles also contain small amounts of other metals, such as about 0.5% w/w zinc and/or about 0.5% w/w copper.

In some examples, the silver microparticles in the disclosed compositions have at least one dimension (such as average diameter) of about 0.1 µm to about 700 µm (for example, about 1 µm to about 100 µm, about 5 µm to about 80 µm, or about 2 to 20 µm). In one non-limiting example, the silver microparticles have an average diameter of about 10 µm. In a particular example, the silver microparticles are MicroSilver BG™ microparticles (BioEpiderm, Nuremberg, Germany).

In some embodiments, the compositions disclosed herein have a neutral pH. For example, the pH of the composition is about 6.5 to about 7.5 or about 6.5 to about 7. In some examples, the pH of the composition is about 6.5, about 6.6, about 6.7, about 6.8, about 6.9, about 7.0, about 7.1, about 7.2, about 7.3, about 7.4, or about 7.5. In some examples, the composition has a pH that facilitates gradual release of silver ions from the silver microparticles in the composition.

In particular embodiments, a disclosed composition includes a formulation including about 0.1% silver microparticles (such as 10 µm diameter silver microparticles) suitable for cleansing the ear canal (a "flush" composition) to break up, remove, and/or reduce debris and/or ear wax in the ear canal. In additional embodiments, a disclosed composition includes a formulation including about 0.2% silver microparticles (such as 10 µm diameter silver microparticles) suitable for rinsing the ear canal (a "rinse" composition) to remove debris and/or ear wax from the ear canal. In still further embodiments, a disclosed composition includes a formulation including about 0.4% silver microparticles (such as 10 µm diameter silver microparticles) suitable for neutralizing or killing bacteria and/or fungi (a "therapy" composition) in the ear canal. In some examples, the therapy composition (or the silver microparticles included in the therapy composition) remains in contact with the surfaces of the ear canal, gradually releasing silver ions and inhibiting microbial growth and/or viability.

In particular embodiments, the compositions disclosed herein are aqueous solutions. The compositions may also contain additional ingredients, such as one or more pharmaceutically acceptable carriers, buffers, solvents, preservatives, surfactants, excipients, emulsifiers, thickeners, lubricants, humectant, emollient, fragrances, and so on. The disclosed compositions may also include additional therapeutic agents including anti-inflammatory compounds, antibiotics, or antifungals. In particular examples, one or more of the disclosed compositions may include a corticosteroid, such as dexamethasone. In some examples, the therapy composition includes additional therapeutic agents, such as a corticosteroid (for example, dexamethasone). One of skill in the art can select appropriate ingredients and proportions for the desired applications.

In particular examples, the flush composition is an aqueous solution containing 0.1% silver microparticles (such as 0.1% MicroSilver BG™ silver microparticles), alcohol, polysorbate 80, cocamidopropyl betaine, glycerin, propanediol, benzylalcohol, acrylates copolymer, potassium sorbate, sodium hydroxide, and salicylic acid. In other examples, the rinse composition is an aqueous solution containing 0.2% silver microparticles (such as 0.2% MicroSilver BG™ silver microparticles), propanediol, glycerin, benzylalcohol, potassium sorbate, acrylates copolymer, and sodium hydroxide. In further examples, the therapy composition is an aqueous solution containing 0.4% silver microparticles (such as 0.4% MicroSilver BG™ silver microparticles), glycerin, panthenol, propyleneglycol, polyglyceryl-4-caprate, benzylalcohol, acrylates copolymer, ethylhexylglycerin, sodium hydroxide, and *citrus medica* limonum (lemon) peel oil.

IV. KITS

Also disclosed are kits including one or more of the disclosed compositions. For example, kits can include at least one container including a composition containing about 0.1% silver microparticles, at least one container including a composition containing about 0.2% silver microparticles, at least one container including a composition containing about 0.4% silver microparticles, or a combination of two or more thereof. In some examples, the kit includes a container including a composition including about 0.1% silver microparticles, a container including a composition including about 0.2% silver microparticles, and a container including a composition including about 0.4% silver microparticles. The kit may also include instructions for use of the one or more compositions included in the kit.

In one non-limiting example, a kit includes a container including an aqueous solution containing 0.1% silver microparticles (such as 0.1% MicroSilver BG™ silver microparticles), alcohol, polysorbate 80, cocamidopropyl betaine, glycerin, propanediol, benzylalcohol, acrylates copolymer, potassium sorbate, sodium hydroxide, and salicylic acid ("flush" composition); a container including an aqueous solution containing 0.2% silver microparticles (such as 0.2% MicroSilver BG™ silver microparticles), propanediol, glycerin, benzylalcohol, potassium sorbate, acrylates copolymer, and sodium hydroxide ("rinse" composition); and a container including an aqueous solution containing 0.4% silver microparticles (such as 0.4% MicroSilver BG™ silver microparticles), glycerin, panthenol, propyleneglycol, polyglyceryl-4-caprate, benzylalcohol, acrylates copolymer, ethylhexylglycerin, sodium hydroxide, and *citrus medica* limonum (lemon) peel oil ("therapy" composition).

The kit may optionally include device(s) for application of the composition(s), such as droppers and/or syringes. In some examples, the container including the composition (such as the flush, rinse, and/or therapy composition) is a dropper bottle. In other examples, separate droppers are included in the kit. In particular examples, the kit includes a syringe (such as a 3-10 ml syringe) and one or more syringe tips (such as 1-60 or 7-30 syringe tips). The syringe tips are disposable single-use tips, which reduce risk of recontamination of the affected ear on subsequent applications.

The following examples are provided to illustrate certain particular features and/or embodiments. These examples should not be construed to limit the disclosure to the particular features or embodiments described.

Example 1

In Vitro Anti-Microbial Effect of Silver Microparticles

This example describes in vitro effects of silver microparticles on yeast and bacteria.

Cells were plated on agar at an initial cell count of $1 \times 10^7$ cells/ml and treated with SantéNurturing Spray (SantéAnimal Care, Boonton, N.J.) with or without 0.2% silver microparticles (Microsilver BG™, BioEpiderm, Nuremberg, Germany). Treatment with 0.2% silver microparticles resulted in dramatic reduction of the number of colonies in as little as 1 hour for both bacteria and yeast (FIGS. 1A-E).

Example 2

Effect of Silver Microparticle Treatment on Chronic Ear Infection in Dogs

This example describes efficacy of treatment of chronic ear infections in dogs with silver microparticles.

Four dogs with chronic ear infection (Table 2) were treated in an initial study. The dogs were sedated and ears cleaned with a surfactant flush and then with saline and suctioned. A pluronic gel containing 0.2% 10 µm silver microparticles was injected into the ear canal. The treatment was administered 1-3 times at about 2 week intervals. Owners were instructed to administer a spray containing 0.2% silver microparticles daily at home. Compliance with the spray was variable.

TABLE 2

Clinical information on initial study patients

| Patient | Presentation | Culture Results |
| --- | --- | --- |
| 1<br>6 y.o. Weimaraner | Moderately infected left ear; severely infected right ear with ulcerations | Several bacterial strains, about ⅔ of which were methicillin resistant |
| 2<br>11 y.o Springer Spaniel | Otic hemorrhage | *Pseudomonas* |
| 3<br>9 y.o. Beagle | Chronic infection with ulcerations | |
| 4<br>13 y.o. Golden Retriever | Extensive debris in ear | Significant, but not high numbers of organisms |

Figure 2:
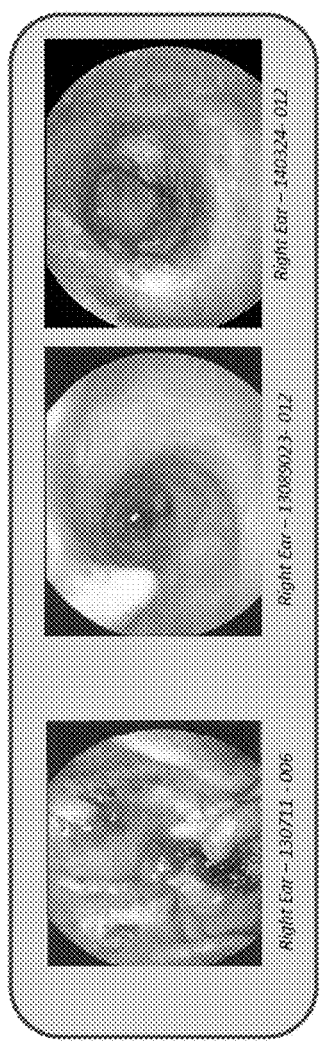
FIG. 2 is a series of otoscopic images of the right ear of patient 1 taken before treatment (left), about 10 weeks after beginning treatment with 0.2% silver microparticles (middle); and at follow up 6 months later (right).

Patient 1 received three treatments with the silver pluronic gel, with spray administered by owner daily. No visual improvement was observed after first two treatments, but owner reported the dog was more comfortable. After the third treatment the ulcerations were cauterized and the spray was continued daily without further treatment. About 10 weeks after the initial treatment improvement was observed in both ears (FIG. 2). The spray was continued every other day with the addition of dexamethasone to reduce biofilm formation.

Patient 2 was treated with silver gel and owner was instructed to use spray daily. At follow up about 6 weeks after treatment, a slight improvement in cultures and appearance of ear were observed; however, owner reported using spray once weekly rather than daily.

Patient 3 was treated with silver gel. Two weeks later, a mild improvement was observed, though there was little change in the cultures. Ulcers were cauterized and ears were treated again. One month later, middle and lower portions of the ear canal looked improved though there were still ulcerations in upper ear canal.

Patient 4 was treated as above. At two week follow up, cultures were negative and mild improvement in appearance was observed. Ears were treated two more times at two week intervals. After final treatment left ear had good appearance and right ear was much better. Owner was instructed to use spray once daily and ears looked much better about one month later.

Overall, these patients would have normally been treated with ear flush, steroid drops (possibly with antibiotics and antifungal drugs), and systemic antibiotics. Patient 4 demonstrated a rapid response. The remaining patients showed moderate improvements, indicating a phase 2 study was warranted. It is important to note that these patients had severe ear infections and demonstrated improvement in this study without the use of antibiotics or antifungals.

Example 3

Three-Step Silver Microparticle Treatment for Ear Infection in Dogs

This example describes a three-step system for treating ear infection in dogs with silver microparticles.

Ten dogs with chronic ear infections (over 7 years with infection) which were not responsive to antibiotics were treated with a three step system including a flush, rinse, and therapy system (Table 3). The dogs were sedated for the initial treatment. First, a liberal amount of flush composition was applied to the ear canal. The ear was massaged from the outside to break up debris and a cotton ball was used to clean the outer ear and to remove any visible debris. This step was repeated. Next, a liberal amount of rinse composition was applied to the ear canal. A cotton ball was used to clean the outer ear and periphery of the canal. Finally, the therapy composition was injected into the ear canal with a syringe and massaged externally to work the solution into the ear canal (1-2 cc for dogs <14 pounds; 2-3 cc for dogs 14-40 pounds; 3-4 cc for dogs 40-100 pounds; and >4 cc for dogs >100 pounds). The patient was then sent home with instructions to utilize the flush, rinse, and therapy compositions as instructed (for example, every other day).

TABLE 3

Three solution system for treating ear infection

| Solution | MicroSilver BG ™ | Other ingredients |
| --- | --- | --- |
| Flush | 0.1% | Aqua, Alcohol, Polysorbate 80, Cocamidopropyl Betaine, Glycerin, Propanediol, Benzylalcohol, Acrylates Copolymer, Potassium Sorbate, Sodium Hydroxide, Salicylic Acid |
| Rinse | 0.2% | Aqua, Propanediol, Glycerin, Benzylalcohol, Potassium Sorbate, Acrylates Copolymer, Sodium Hydroxide |
| Therapy | 0.4% | Aqua, Glycerin, Panthenol, Propyleneglycol, Polyglyceryl-4-Caprate, Benzylalcohol, Acrylates Copolymer, Ethylhexylglycerin, Sodium Hydroxide, *Citrus Medica Limonum* (Lemon) Peel Oil |

Figure 3:
FIG. 3 is a series of otoscope images of patient 1's left ear prior to initial treatment and following completion of initial application of flush, rinse, and therapy compositions.
Figure 3:
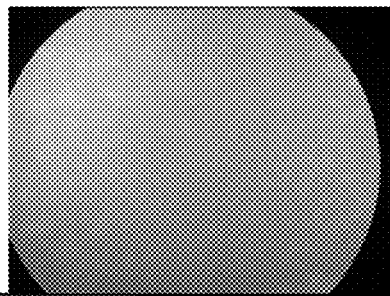
Figure 3:
Figure 4:
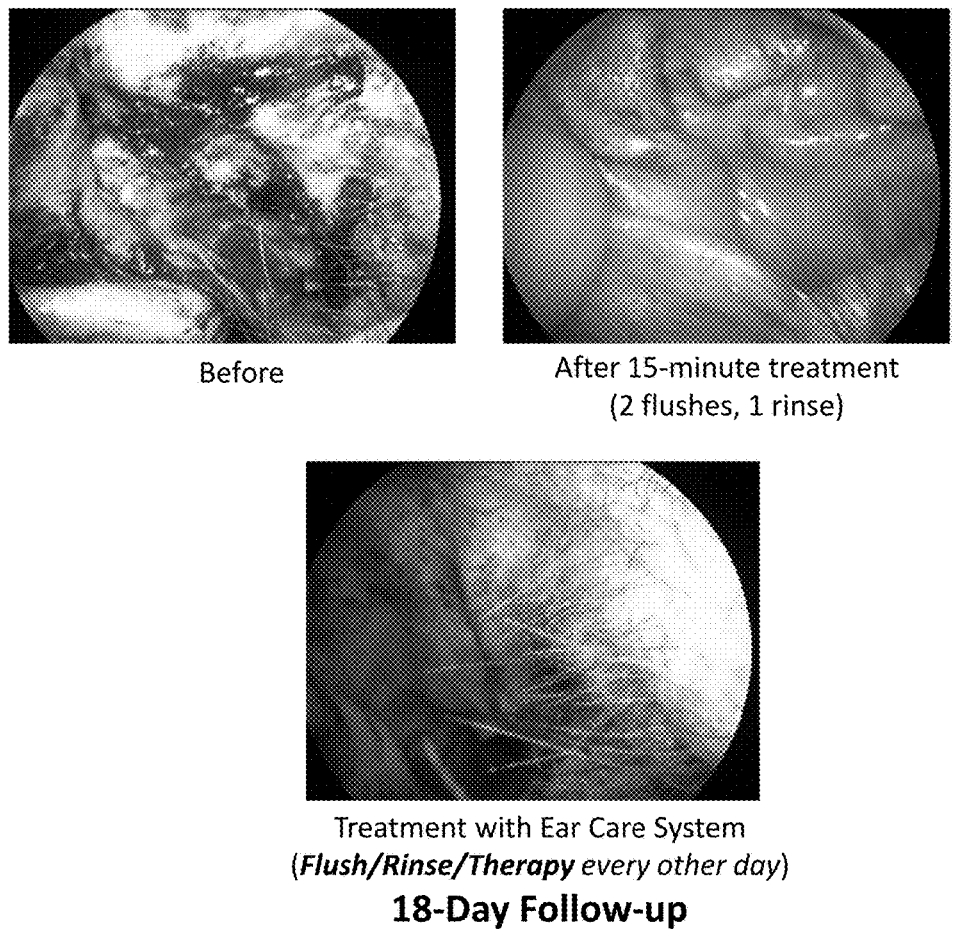
FIG. 4 is a series of otoscope images of patient 1's right ear prior to treatment, following completion of the initial flush and rinse composition application, and after 18 days with treatment with flush, rinse, and therapy compositions every other day.

As an example, patient 1 from Example 2 was treated with the flush, rinse, therapy system. FIG. 3 shows otoscopes of patient 1's left ear prior to the initial treatment and following completion of the flush, rinse, and therapy composition applications. FIG. 4 shows otoscopes of patient 1's right ear prior to treatment, following completion of the initial flush (2×) and rinse (1×) treatments, and at the 18 day follow up appointment. The patient's ear was markedly improved on follow up.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A kit for treating an ear infection comprising:
   (a) a first container comprising a first aqueous solution comprising about 0.1% silver microparticles, wherein the solution has a pH of 6.5 to 7.5;
   (b) a second container comprising a second aqueous solution comprising about 0.2% silver microparticles, wherein the solution has a pH of 6.5 to 7.5; and
   (c) a third container comprising a third aqueous solution comprising about 0.4% silver microparticles, wherein the solution has a pH of 6.5 to 7.5,
   wherein the first, second and third aqueous solutions are applied to a subject to treat the ear infection.

2. The kit of claim 1, wherein the first aqueous solution further comprises one or more of alcohol, polysorbate 80, cocamidopropyl betaine, glycerin, propanediol, benzylalcohol, acrylates copolymer, potassium sorbate, sodium hydroxide, and salicylic acid.

3. The kit of claim 1, wherein the second aqueous solution further comprises one or more of propanediol, glycerin, benzylalcohol, potassium sorbate, acrylates copolymer, and sodium hydroxide.

4. The kit of claim 1, wherein the third aqueous solution further comprises one or more of glycerin, propyleneglycol, polyglyceryl-4-caprate, benzylalcohol, acrylates copolymer, ethylhexylglycerin, sodium hydroxide, and *citrus medica limonum* (lemon) peel oil.

5. The kit of claim 1, wherein the first aqueous solution further comprises alcohol, polysorbate 80, cocamidopropyl betaine, glycerin, propanediol, benzylalcohol, acrylates copolymer, potassium sorbate, sodium hydroxide, and salicylic acid.

6. The kit of claim 1, wherein the second aqueous solution further comprises propanediol, glycerin, benzylalcohol, potassium sorbate, acrylates copolymer, and sodium hydroxide.

7. The kit of claim 1, wherein the third aqueous solution further comprises glycerin, propyleneglycol, polyglyceryl-4-caprate, benzylalcohol, acrylates copolymer, ethylhexylglycerin, sodium hydroxide, and *citrus medica* limonum (lemon) peel oil.

8. A method of treating an ear infection in a subject comprising applying to an ear canal of the subject an effective amount of the first, second, and third aqueous solutions of the kit of claim 1.

9. The method of claim 8, wherein each of the first aqueous solution, the second aqueous solution, and the third aqueous solution are sequentially applied to the ear canal of the subject.

10. The method of claim 8, wherein the pH of each of the first aqueous solution, the second aqueous solution, and the third aqueous solution is about pH 7.

11. The method of claim 8, wherein the silver microparticles comprise an average particle size of about 10 μm.

12. The method of claim 8, wherein the first aqueous solution further comprises one or more of alcohol, polysorbate 80, cocamidopropyl betaine, glycerin, propanediol, benzylalcohol, acrylates copolymer, potassium sorbate, sodium hydroxide, and salicylic acid.

13. The method of claim 8, wherein the second aqueous solution further comprises one or more of propanediol, glycerin, benzylalcohol, potassium sorbate, acrylates copolymer, and sodium hydroxide.

14. The method of claim 8, wherein the third aqueous solution further comprises one or more of glycerin, propyleneglycol, polyglyceryl-4-caprate, benzylalcohol, acrylates copolymer, ethylhexylglycerin, sodium hydroxide, and *citrus medica* limonum (lemon) peel oil.

15. The method of claim 8, wherein the third aqueous solution further comprises one or more corticosteroids.

16. The method of claim 8, wherein the first aqueous solution, the second aqueous solution, and the third aqueous solution are applied to the ear canal of the subject once daily, every other day, or once weekly.

17. The method of claim 8, wherein the subject is a veterinary subject.

18. The method of claim 17, wherein the veterinary subject is a dog or cat.

* * * * *